(12) United States Patent
Chong

(10) Patent No.: US 10,206,567 B2
(45) Date of Patent: Feb. 19, 2019

(54) DUAL WAVELENGTH RESAMPLING SYSTEM AND METHOD

(71) Applicant: SANTEC CORPORATION, Komaki, Aichi (JP)

(72) Inventor: Changho Chong, Los Altos, CA (US)

(73) Assignee: SANTEC CORPORATION, Komaki (JP)

( * ) Notice: Subject to any disclaimer, the term of this patent is extended or adjusted under 35 U.S.C. 154(b) by 0 days.

(21) Appl. No.: 15/648,239

(22) Filed: Jul. 12, 2017

(65) Prior Publication Data
US 2019/0014983 A1    Jan. 17, 2019

(51) Int. Cl.
*A61B 3/10* (2006.01)
*G01B 9/02* (2006.01)

(52) U.S. Cl.
CPC .......... *A61B 3/102* (2013.01); *G01B 9/02008* (2013.01); *G01B 9/02091* (2013.01)

(58) Field of Classification Search
CPC .......... A61B 3/14; A61B 3/0025; A61B 3/12; A61B 3/102; A61B 3/0058
USPC ....................................... 351/206
See application file for complete search history.

(56) References Cited

U.S. PATENT DOCUMENTS

| | | |
|---|---|---|
| 4,466,699 A | 8/1984 | Droessler et al. |
| 5,022,745 A | 6/1991 | Zayhowski et al. |
| 5,319,668 A | 6/1994 | Luecke |
| 5,372,135 A | 12/1994 | Mendelson et al. |
| 5,430,574 A | 7/1995 | Tehrani |
| 5,537,162 A | 7/1996 | Hellmuth et al. |
| 5,561,523 A | 10/1996 | Blomberg et al. |
| 5,982,963 A | 11/1999 | Feng et al. |
| 6,070,093 A | 5/2000 | Oosta et al. |

(Continued)

FOREIGN PATENT DOCUMENTS

| | | |
|---|---|---|
| DE | 10 2011 114 797 A1 | 4/2013 |
| JP | 2006-202543 A | 8/2006 |

(Continued)

OTHER PUBLICATIONS

Changho Chong, et al. "Large Coherence Length Swept Source for Axial Length Measurement of the Eye." Applied Optics 48:10 (2009): D145-150.

(Continued)

*Primary Examiner* — Mohammed A Hasan
(74) *Attorney, Agent, or Firm* — Foley & Lardner LLP

(57) ABSTRACT

An optical coherence tomography (OCT) system combining multiple wavelengths is generally described. In an example, the OCT system includes multiple wavelength swept light sources. The system further includes an interferometer into which light from the light sources is directed and a detector configured to produce an imaging sample signal based on light received from the interferometer. The system also includes a splitter configured to split light from at least one of light sources before the light reaches the interferometer. The system also includes a wavelength reference filter having an equal interval frequency comb and a signal processing circuit. The wavelength reference filter is configured to produce a sequential clock waveform from light received from the splitter, and the signal processing circuit is configured to resample the imaging sample signal based on the sequential clock waveform.

20 Claims, 5 Drawing Sheets

(56) References Cited

U.S. PATENT DOCUMENTS

| | | |
|---|---|---|
| 6,111,645 A | 8/2000 | Tearney et al. |
| 6,134,003 A | 10/2000 | Tearney et al. |
| 6,160,826 A | 12/2000 | Swanson et al. |
| 6,275,718 B1 | 8/2001 | Lempert |
| 6,282,011 B1 | 8/2001 | Tearney et al. |
| 6,373,632 B1 | 4/2002 | Flanders |
| 6,421,164 B2 | 7/2002 | Tearney et al. |
| 6,485,413 B1 | 11/2002 | Boppart et al. |
| 6,501,551 B1 | 12/2002 | Tearney et al. |
| 6,564,087 B1 | 5/2003 | Pitris et al. |
| 6,725,073 B1 | 4/2004 | Motamedi et al. |
| 7,099,358 B1 | 8/2006 | Chong |
| 7,231,243 B2 | 6/2007 | Tearney et al. |
| 7,323,680 B2 | 1/2008 | Chong |
| 7,324,214 B2 | 1/2008 | De Groot et al. |
| 7,352,783 B2 | 4/2008 | Chong |
| 7,382,809 B2 | 6/2008 | Chong et al. |
| 7,388,891 B2 | 6/2008 | Uehara et al. |
| 7,400,410 B2 | 7/2008 | Baker et al. |
| 7,414,779 B2 | 8/2008 | Huber et al. |
| 7,428,057 B2 | 9/2008 | De Lega et al. |
| 7,489,713 B2 | 2/2009 | Chong et al. |
| 7,701,588 B2 | 4/2010 | Chong |
| 7,725,169 B2 | 5/2010 | Boppart et al. |
| 7,835,010 B2 | 11/2010 | Morosawa et al. |
| 7,865,231 B2 | 1/2011 | Tearney et al. |
| 7,869,057 B2 | 1/2011 | De Groot |
| 7,884,945 B2 | 2/2011 | Srinivasan et al. |
| 7,961,312 B2 | 6/2011 | Lipson et al. |
| 8,036,727 B2 | 10/2011 | Schurman et al. |
| 8,115,934 B2 | 2/2012 | Boppart et al. |
| 8,315,282 B2 | 11/2012 | Huber et al. |
| 8,405,834 B2 | 3/2013 | Srinivasan et al. |
| 8,500,279 B2 | 8/2013 | Everett et al. |
| 8,625,104 B2 | 1/2014 | Izatt et al. |
| 8,690,328 B1 | 4/2014 | Chong |
| 8,690,330 B2 | 4/2014 | Hacker et al. |
| 9,163,930 B2 | 10/2015 | Buckland et al. |
| 2002/0163948 A1 | 11/2002 | Yoshida et al. |
| 2005/0171438 A1 | 8/2005 | Chen et al. |
| 2005/0201432 A1 | 9/2005 | Uehara et al. |
| 2005/0213103 A1 | 9/2005 | Everett et al. |
| 2006/0105209 A1 | 5/2006 | Thyroff et al. |
| 2006/0109872 A1 | 5/2006 | Sanders |
| 2006/0215713 A1 | 9/2006 | Flanders et al. |
| 2007/0040033 A1 | 2/2007 | Rosenberg |
| 2007/0076217 A1 | 4/2007 | Baker et al. |
| 2007/0081166 A1 | 4/2007 | Brown et al. |
| 2007/0133647 A1* | 6/2007 | Daiber .................. H01S 5/026 372/99 |
| 2007/0141418 A1 | 6/2007 | Ota et al. |
| 2007/0263226 A1 | 11/2007 | Kurtz et al. |
| 2007/0291277 A1 | 12/2007 | Everett et al. |
| 2008/0269575 A1 | 10/2008 | Iddan |
| 2009/0022181 A1 | 1/2009 | Atkins et al. |
| 2009/0103050 A1 | 4/2009 | Michaels et al. |
| 2009/0169928 A1 | 7/2009 | Nishimura et al. |
| 2009/0247853 A1 | 10/2009 | Debreczeny |
| 2009/0268020 A1 | 10/2009 | Buckland et al. |
| 2009/0290613 A1 | 11/2009 | Zheng et al. |
| 2010/0157308 A1 | 6/2010 | Xie |
| 2010/0246612 A1 | 9/2010 | Shimizu |
| 2010/0284021 A1 | 11/2010 | Hacker |
| 2011/0112385 A1 | 5/2011 | Aalders |
| 2011/0235045 A1 | 9/2011 | Koerner |
| 2011/0255054 A1 | 10/2011 | Hacker et al. |
| 2011/0299034 A1 | 12/2011 | Walsh et al. |
| 2012/0026466 A1 | 2/2012 | Zhou et al. |
| 2012/0136259 A1 | 5/2012 | Milner et al. |
| 2012/0188555 A1 | 7/2012 | Izatt et al. |
| 2014/0051952 A1 | 2/2014 | Reichgott et al. |
| 2014/0111774 A1 | 4/2014 | Komine |
| 2014/0228681 A1 | 8/2014 | Jia et al. |
| 2014/0268163 A1 | 9/2014 | Milner et al. |
| 2014/0293290 A1* | 10/2014 | Kulkarni ............ G01B 9/02091 356/479 |
| 2014/0336479 A1 | 11/2014 | Ando |
| 2015/0348287 A1 | 12/2015 | Yi et al. |
| 2016/0178346 A1* | 6/2016 | Kulkarni ............ G01B 9/02044 356/479 |

FOREIGN PATENT DOCUMENTS

| | | |
|---|---|---|
| JP | 2008-188047 | 8/2008 |
| JP | 2010-172538 | 8/2010 |
| WO | WO-2012/075126 A2 | 6/2012 |
| WO | WO-2013/168149 A1 | 11/2013 |
| WO | WO-2015/121756 A2 | 8/2015 |

OTHER PUBLICATIONS

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

Dai et al., "Optical coherence tomography for whole eye segment imaging," Optics Express, vol. 20, No. 6 (2012) pp. 6109-6115.

Dhalla et al., "Simultaneous swept source optical coherence tomography of the anterior segment and retina using coherence revival," Optics Letters, vol. 37 No. 11, Jun. 1, 2012, pp. 1883-1885.

Dhalla, et al., "Simultaneous swept source optical coherence tomography of the anterior segment and retina using coherence revival," Optics Letters, 2012, vol. 37, No. 11, pp. 1883-1885.

English Translation of the International Search Report and Written Opinion on International Application No. PCT/EP2009/009189, dated Apr. 6, 2010, 12 pages.

F. Lexer et al., "Wavelength-tuning interferometry of intraocular distances," Applied Optics, vol. 36, No. 25, pp. 6548-6553 (Sep. 1, 1997).

Fainman, Y. et al., "Nanophotonics for Information Systems," Information Optics and Photonics (T. Fournel and B. Javidi eds., Springer New York, 2010) pp. 13-37.

International Preliminary Report on Patentability in corresponding application PCT/US2016/035012 dated Dec. 14, 2017.

International Preliminary Report on Patentability in corresponding international application No. PCT/US2015/019299 dated Sep. 22, 2016.

International Preliminary Report on Patentability in corresponding international application No. PCT/US2015/032727 dated Dec. 8, 2016.

International Preliminary Report on Patentability in International appln. No. PCT/IB2015/000808.

International Search Report and Written Opinion dated Aug. 26, 2015 for PCT/US15/32727 (8 pages).

International Search Report and Written Opinion in corresponding application No. PCT/US2016/035012 dated Aug. 18, 2016.

International Search Report and Written Opinion in International Application No. PCT/US2015/19299 dated Nov. 2, 2015 (10 pages).

International Search Report and Written Opinion in PCT/IB2015/000808 dated Oct. 20, 2015 (12 pages).

Jeong et al., "Spectral-domain OCT with dual illumination and interlaced detection for simultaneous anterior segment and retina imaging," Optics Express, vol. 20, Issue 17, pp. 19148-19159 (2012).

Jeong, et al., "Spectral-domain OCT with dual illumination and interlaced detection for simultaneous anterior segment and retina imaging," Optics Express, 2012, vol. 20, Issue 17, pp. 19148-19159.

Jia et al., Split-Spectrum Amplitude-Decorrelation Angiography with Optical Coherence Tomography, Optics Express, vol. 20 No. 4, Feb. 9, 2012, pp. 4710-4725.

Lexer et al., "Wavelength-tuning interferometry of intraocular distances", Applied Optics, vol. 36, No. 25, Sep. 1, 1997, pp. 6548-6553.

Mariampillai et al., Speckle Variance Detection of Microvasculature Using Swept-Source Optical Coherence Tomography, Optics Letters, vol. 33 No. 13, Jul. 1, 2008, pp. 1530-1532.

(56) References Cited

OTHER PUBLICATIONS

Nankivil et al.,"Handheld, rapidly switchable, anterior/posterior segment swept source optical coherence tomography probe," OSA Nov. 1, 2015; vol. 6, No. 11; DOI:10.1364/BOE.6.004516; Biomedical Optics Express 4516-4528.
Non-Final Rejection on U.S. Appl. No. 14/723,325 dated Dec. 7, 2017.
P. Tayebati et al., "Microelectromechanical tunable filter with stable half symmetric cavity," Electronics Letters, vol. 34, No. 20, pp. 1967-1968 (Oct. 1, 1998).
Poddar, et al., "Non-Invasive Glucose Monitoring Techniques: A Review and Current Trends," Oct. 31, 2008, pp. 1-47.
Sarlet, G. et al., "Wavelength and Mode Stabilization of Widely Tunable SG-DBR and SSG-DBR Lasers," IEEE Photonics Technology Letters, vol. 11, No. 11, Nov. 1999, pp. 1351-1353.
Segawa, Toru et al., "Semiconductor Double-Ring-Resonator-Coupled Tunable Laser for Wavelength Routing," IEEE Journal of Quantum Electronics, vol. 45, No. 7, Jul. 2009, pp. 892-899.
Sergie Ortiz, et al. "Corneal Topography From Spectral Optical Coherence Tomography (SOCT)." Biomedical Optics Express 2:12, (2011):3232-3247.
U.S. Notice of Allowance on U.S. Appl. No.14/601,945 dated Sep. 13, 2016.
U.S. Office Action on dated Sep. 12, 2013.
U.S. Office Action on dated Aug. 19, 2015.
U.S. Office Action on U.S. Appl. No. 14/601,945 dated Mar. 2, 2016.
U.S. Office Action on U.S. Appl. No. 14/613644 dated Jun. 8, 2016.
U.S. Office Action on U.S. Appl. No. 14/641,200 dated Mar. 14, 2016.
U.S. Office Action on U.S. Appl. No. 14/641,200 dated Dec. 7, 2015.
U.S. Office Action on U.S. Appl. No. 14/723,325 dated Nov. 18, 2016.
U.S. Office Action on U.S. Appl. No. 15/202,925 dated Jul. 27, 2017.
Chopra et al., Topographical Thickness of the Skin in the Human Face, Aesthetic Surgery Journal, vol. 35(8), 2015, pp. 1007-1013.
Final Office Action on U.S. Appl No. 14/723,325 dated Jul. 26, 2018.
Non-Final Office Action on U.S. Appl. No. 15/086,520 dated Aug. 6, 2018.
Non-Final Office Action on U.S. Appl. No. 15/139,579 dated Jul. 17, 2018.
U.S. Notice of Allowance on U.S. Appl. No. 15/202,925 dated May 17, 2018.
U.S. Office Action on U.S. Appl. No. 15/630654 dated Apr. 4, 2018.

* cited by examiner

DUAL WAVELENGTH RESAMPLING SYSTEM AND METHOD

BACKGROUND

The following description is provided to assist the understanding of the reader. None of the information provided or references cited is admitted to be prior art.

Optical coherence tomography (OCT) is an imaging technique. OCT imaging techniques are often used in a medical setting. The techniques are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

OCT is often accomplished with the use of an interferometer. An interferometer utilizes light that is reflected back from a sample and a reference light. The reference light is generally configured to travel a similar distance as light that is reflected back from the sample. The light from the sample and the reference light can be combined in such a way that gives rise to an interference pattern. That is, the light from the sample and the reference light will either constructively or destructively interfere with each other. The level of interference that occurs indicates the reflectivity of areas of the sample, such that structures within the sample may be identified and imaged.

SUMMARY

In an embodiment, the present technology provides an improved optical coherence tomography (OCT) system combining two wavelengths capable, for example, of simultaneously imaging the anterior chamber and retina of an eye. In an illustrative embodiment, the OCT system includes a first light source configured to emit a first beam having a first wavelength and a second light source configured to emit a second beam having a second wavelength. The system further includes an interferometer into which the first beam and the second beam are configured to be directed. The interferometer includes a reference path and an interferometer sample path. The system further includes a detector configured to compare light from the reference path with light from the interferometer sample path and product an imaging sample signal based on the comparison, and a splitter configured to split light from at least one of the first light source and the second light source. The splitter is located on a light path between the first light source and the interferometer. The system also includes a wavelength reference filter having an equal interval frequency comb and a signal processing circuit. The wavelength reference filter is configured to produce a sequential clock waveform from light received from the splitter, and the signal processing circuit is configured to resample the imaging sample signal based on the sequential clock waveform.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
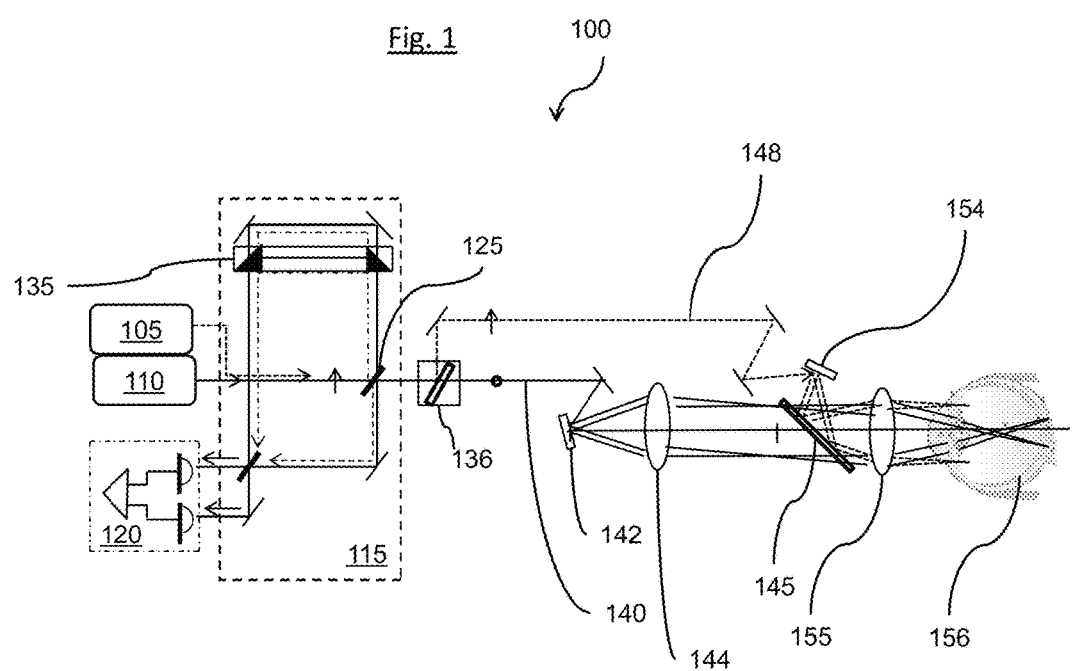
FIG. 1 depicts a representation of an optical coherence tomography (OCT) system combining two wavelengths from two wavelength swept light sources in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an improved optical coherence tomography (OCT) system capable of combining two wavelengths from two different light sources for imaging multiple areas of a patient. The system is additionally configured to provide resampling that requires only one additional input channel by combining two sets of clock waveforms in the optical domain.

Interference tomographic measurement techniques generally have two types: time domain tomographic measurement and frequency domain tomographic measurement. Frequency domain tomographic measurements have two primary types: a spectrometer type and tunable light source type. An example tunable light source type irradiates an imaging area with irradiation light while continuously changing the wavelength of irradiation light. The system creates an interference signal with an interferometer by allowing reference light to interfere with reflected light returned from a different depth in the imaging area. The system can then analyze a frequency component of the interference signal to obtain an image. Images of very high resolution can be created based on frequency analysis of the interference signal.

In an optical coherence tomography device, it is necessary to obtain points at a regular frequency interval according to resolution of the image in one wavelength scan and set them as timing signals for a Fourier transformation. The timing signal may be referred to as a k trigger. An interval of a trigger signal corresponds to the range of observed depth, and as the interval is made smaller, deeper analysis can be performed. The interval of a trigger signal should be a regular frequency interval. If the interval of the trigger signal is not an equal frequency interval, wavelength scanning can become nonlinear resulting in generation of an image with distortion or noise. Traditional wavelength-tunable laser light sources have suffered from wavelengths that do not linearly vary with respect to time, and thus, a trigger signal cannot be easily obtained at a regular frequency interval. To solve such problems, resampling of the interference signal may be performed to evenly sample the signal in the frequency domain. Systems that incorporate multiple, separate light sources that have different nonlinear sweeps have traditionally required independent resampling. As a result, numerous input channels and complex processing would be required to perform the independent resampling of multiple light sources in a system that utilizes multiple wavelengths to simultaneously image multiple areas of an imaging area, e.g., an eye. Discussed in additional detail below is a resampling scheme that requires only one additional input channel by combining multiple sets of clock waveforms in the optical domain.

An example system that incorporates multiple, separate light sources that have different nonlinear sweeps is discussed in U.S. Provisional Patent App. No. 62/169,230, filed Jun. 1, 2015, which is incorporated herein by reference in its entirety. Such a system is capable of imaging both the anterior chamber and the retina of an eye simultaneously by superimposing two light paths of different wavelength ranges suitable for eye imaging into one path. Such a system can also utilize a single detector and interferometer to detect two imaging ranges. Previously, systems have utilized multiple interferometers and multiple photo-detectors in order to image two samples at once. The methods and systems disclosed herein may use a single interferometer and photodetector, greatly decreasing the cost, complexity, and size of an OCT system designed to scan multiple samples at once.

In addition, methods and systems disclosed herein advantageously also do not utilize complex mechanisms to adjust the focus and incidence angle of a single beam in order to realize multiple imaging ranges. Previously, systems may have used only a single light source for scanning two different samples. However, such systems traditionally utilized complex switchable or adjustable lenses to adjust a single beam in order to switch between multiple imaging ranges. Such a configuration is complex, has many moving parts, and may be quite large. Further, such a configuration may not allow simultaneous and real time imaging of multiple imaging ranges. The methods and systems disclosed herein advantageously reduce the number of components utilized for multiple imaging ranges and allows for simultaneous and real time imaging of multiple imaging ranges. For example, the systems and methods disclosed herein can achieve real time imaging of two imaging ranges, such as an anterior chamber of an eye and the retinal area of an eye.

In an illustrative embodiment, two wavelength swept light sources are used to emit two beams with different wavelengths (or different bands of wavelength). The outputs of the two light sources are combined into an interferometer. The interferometer includes a reference path and a sample path. The sample path is a path through which the beams are transmitted to be reflected off the sample (e.g., an eye). The reference path is a separate path through which the beams are reflected to have the same optical length as the sample path, such that the interferometer can generate an accurate image of the sample.

In an embodiment, light from each of the two wavelength swept light sources is split via a respective splitter at a location between the wavelength swept light sources and the interferometer. In this way, the light from each of the two wavelength swept light sources may be split before it is combined and passed into the interferometer. A portion of the split light from each wavelength swept light source is passed through respective wavelength reference filters that each have equal interval frequency combs. The light output from each of the respective wavelength reference filters is combined at a combiner to generate sequential clock waveforms that correspond to alternately swept wavelength ranges for the two wavelength swept light sources. The generated sequential clock waveforms are passed to a photodiode that converts the waveform to an electrical signal for input into a signal processing circuit that uses the signal for resampling of the sample signals received from the interferometer prior to application of a Fourier transform to the sample signals.

In another implementation, the light from each of the two wavelength swept light sources may be combined into a single light path before being split and passed to a wavelength reference filter. Such an implementation may utilize only a single wavelength reference filter having an equal interval frequency comb. The light output from the respective wavelength reference filter is used to generate sequential clock waveforms that correspond to alternately swept wavelength ranges for the two wavelength swept light sources. The generated sequential clock waveforms are again passed to a photodiode that converts the waveform to an electrical signal for input into a signal processing circuit that uses the signal for resampling of the sample signals received from the interferometer prior to application of a Fourier transform to the sample signals.

The sample signals generated by a detector (which receives an output from the interferometer) are passed to the signal processing circuit. The signal processing circuit can analyze the received sample signals alternately for different time slots based on the generated sequential clock waveforms and a trigger signal received from a driver circuit. In other words, the processor converts the two imaging ranges into two images by selecting specific time slots of the detected signal based on generated sequential clock waveforms and the trigger signal. The processor will thus recognize a first imaging range when a first beam is emitted to image the sample from the first wavelength swept light source, and the processor will recognize a second imaging range when a second beam is emitted to image the sample from the second wavelength swept light source.

FIG. 1 depicts a representation of an optical coherence tomography (OCT) system 100 combining two wavelengths from two wavelength swept light sources in accordance with an illustrative embodiment. In alternative embodiments, fewer, additional, and/or different elements may be present. The OCT system includes a first wavelength swept light source 105 and a second wavelength swept light source 110. The first wavelength swept light source 105 emits a first beam 148 having a first wavelength. In FIG. 1, the first beam 148 is shown with dashed lines to differentiate it from a second beam 140. The second beam 140 is emitted by the second wavelength swept light source 110 and has a second wavelength. The first beam 148 and the second beam 140 are combined and directed into an interferometer 115. The interferometer includes a reference path and an interferometer sample path. The first beam 148 and the second beam 140 from the first light source 105 and the second light source 110 pass through the interferometer 115 to a mirror 125. The mirror 125 here is a half-mirror that reflects some of the light that hits it, but not all light. Accordingly, some of the first beam 148 and the second beam 140 are reflected into the reference path. The reference path includes two different paths that correspond with a first sample path length and a second sample path length. That is, the reference path will change depending on which part of the sample is being imaged (and subsequently which sample path is being utilized).

Accordingly, when the first sample path is being utilized with the first beam 148 to measure an anterior segment of an eye 156, the reference path is longer. When the second sample path is being utilized with the second beam 140 to measure a retinal area of the eye 156, a path length switch 135 is activated to shorten the reference path, which corresponds to the difference in path length between the first sample path and the second sample path. In an alternative embodiment, the reference path (and the shortened reference path when the path length switch 135 is activated) may be variable in order to provide depth scanning of the eye 156. In an alternative embodiment, instead of having a path length switch 135, the difference in path length between a reference path for the first beam 148 and a reference path for the second beam 140 may be pre-adjusted or predetermined in order to have relative offset/non-offset of depth ranges between the anterior chamber and retinal areas of the eye.

When the first beam 148 or the second beam 140 are reflected back from the first sample, they are reflected by the mirror 125 into the interferometer sample path. The light from the reference path and the interferometer sample path are combined and are received by a balanced photo-detector 120, from which two images of the sample can be generated.

The first beam 148 and the second beam 140 output from the interferometer 115 arrive at a beam splitter 136. The beam splitter 136 divides the first beam 148 into a first sample path and the second beam 140 into a second sample path. To do so, the beam splitter 136 reflects or transmits the wavelength band of the first beam 148 but does not reflect or transmit the wavelength band of the second beam 140 (see discussion of FIG. 2 below). On the return path, when the first beam 148 and the second beam 140 have been reflected or backscattered, the beam splitter 136 acts as a combiner.

Accordingly, the first beam 148 is reflected into a first sample path. The first beam 148 is reflected off of a scan mirror 154 that is configured to direct the first beam 148 onto a beam splitter 145, which in turn reflects or transmits the first beam 148 into the lens 155 such that an anterior chamber of the eye 156 may be imaged. Any light of the first beam 148 that is backscattered and/or reflected can return to the interferometer along the same first sample path until it is recombined with the second beam 140 at the beam splitter 136.

After passing through the beam splitter 136, the second beam 140 passes through the second sample path onto a scan mirror 142 such that the second beam 140 is a collimating beam with a convergent scanning pattern to scan the retinal area of the sample. The second beam 140 passes through the lens 144 and passes through the beam splitter 145 without being reflected. In this way, the first beam 148 and the second beam 140 are combined onto a common axis so that each beam may scan the same sample (here the eye 156). The second beam 140 also passes through the lens 155. Any light from the second beam 140 that is reflected or backscattered passes back through the second sample path where it will be recombined with the first beam 148 at the beam splitter 136.

Figure 2:
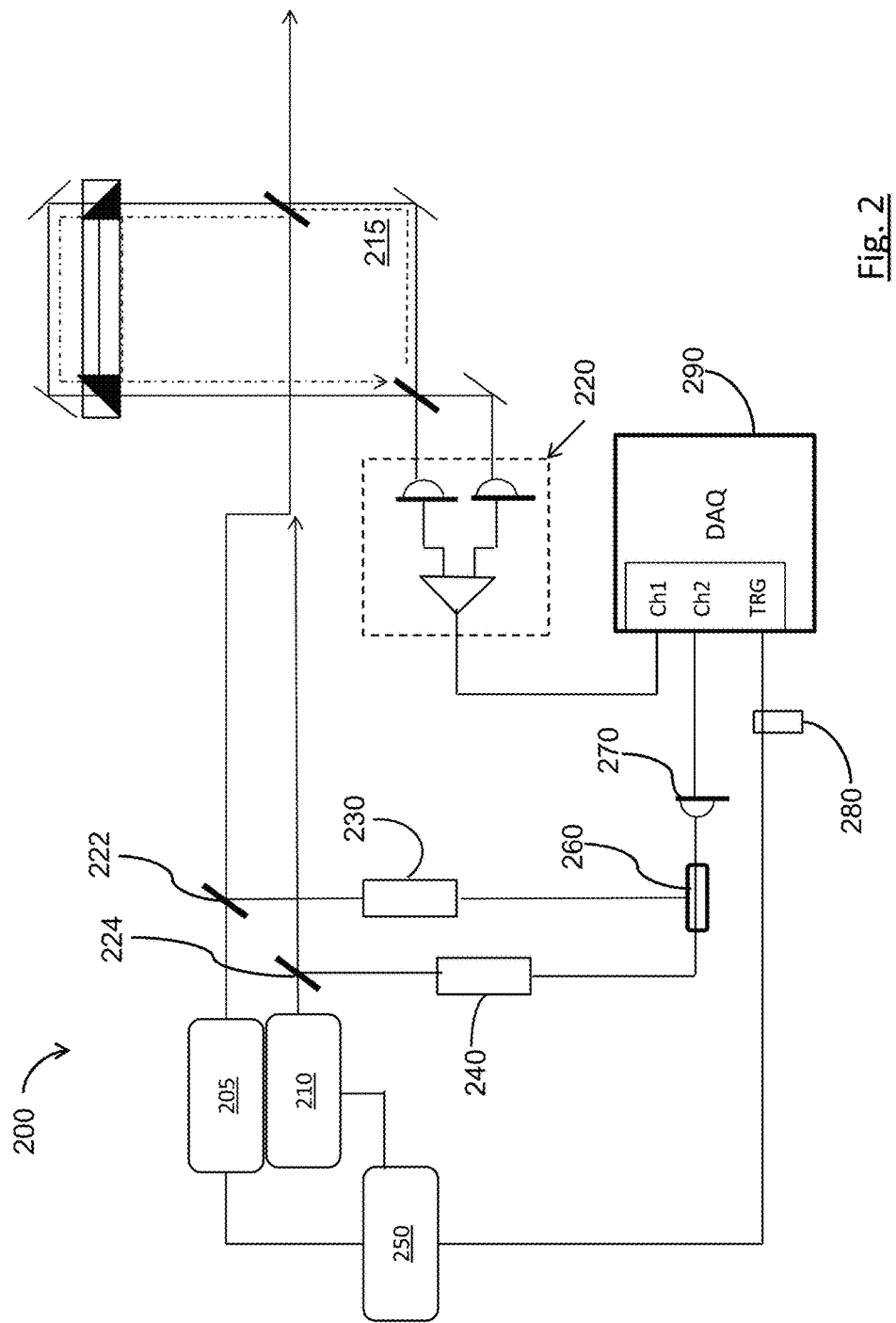
FIG. 2 depicts a representation of an OCT system having two wavelength swept light sources and two wavelength reference filters in accordance with an illustrative embodiment.

FIG. 2 depicts a representation of an OCT system 200 having two wavelength swept light sources 205 and 210 and two wavelength reference filters 230 and 240 in accordance with an illustrative embodiment. In alternative embodiments, fewer, additional, and/or different elements may be present. The first wavelength swept light source 205 emits a first beam having a first wavelength, and the second wavelength swept light source 210 emits a second beam having a second wavelength. In an example embodiment, the first wavelength is 1.06 microns and the second wavelength is 1.31 microns. In additional embodiments, alternative wavelengths may be used based on the imaging requirements of the particular application. The first beam and the second beam are combined and directed into an interferometer 215 which includes a reference path and a sample path. The first and second beams are directed via respective sample paths to an imaging sample, e.g., an eye. Light from the first and second beams that is backscattered and/or reflected from the eye returns to the interferometer along the respective sample paths and is output from the interferometer 215 to a detector 220. Light from the reference path is also output from the interferometer 215 to the detector 220. The detector 220 compares the light from the reference path to the light from the sample paths and outputs a signal based on the comparison. The signal output form the detector 220 is sent to an input channel Ch1 of a signal processing circuit 290. In an embodiment, the signal processing circuit 290 is a data acquisition (DAQ) hardware that interfaces between the signal received from the detector 220 and a computer processing device.

The OCT system 200 further includes a splitter 222 and a splitter 224. Splitter 222 is positioned between an output of the first wavelength swept light source 205 and a location at which the first beam from the first wavelength swept light source 205 is combined with the second beam from the second wavelength swept light source 210. Similarly, splitter 224 is positioned between an output of the second wavelength swept light source 210 and a location at which the first beam from the first wavelength swept light source 205 is combined with the second beam from the second wavelength swept light source 210. The splitter 222 splits a portion of the first beam onto a separate path to a wavelength reference filter 230, and the splitter 224 splits a portion of the second beam onto a separate path to a wavelength reference filter 240. In an implementation, the splitters 222 and 224 split only a small portion of the respective first and second beams on the separate paths while allowing a majority of the respective first and second beams to pass to the interferometer 215. For example, in one implementation, approximately ten percent of the light on the first and second beams is passed to the wavelength reference filters 230 and 240, respectively, and approximately ninety percent of the light on the first and second beams is passed to the interferometer 215. In other implementations, different percentages of light may be split by splitters 222 and 224 based on the design needs of the imaging application.

The wavelength reference filters 230 and 240 each have equal interval frequency combs. Accordingly, the light output from the wavelength reference filters 230 and 240 is equally-spaced in the frequency domain, thus providing equal frequency intervals with which to resample signals received from the detector 220. In an embodiment, the wavelength reference filters 230 and 240 may include a Fabry-Perot Etalon filter, a Mach-Zehnder filter, or any other suitable filter known to those of skill in the art. The outputs from the wavelength reference filters 230 are combined at a combiner 260 and passed to a photodiode 270 to generate sequential clock waveforms having regular, equal frequency intervals. In an embodiment, the combiner 260 may include a coupler or dichroic wavelength division multiplexing (WDM) filter. The sequential clock waveforms are generated by the wavelength reference filters 230 and 240 from the portion of the first and second beams that is split by splitters 222 and 224 and passed through the wavelength reference filters 230 and 240. The sequential clock waveforms correspond to alternately swept wavelength ranges of the first and second wavelength swept light sources 205 and 210. An input channel Ch2 of the signal processing circuit 290 is connected to the output of the photodiode 270 such that the generated sequential clock waveforms are received at the input channel Ch2 of the signal processing circuit 290.

The OCT system 200 also includes a driver circuit 250 that is communicatively coupled to the first wavelength swept light source 205 and the second wavelength swept light source 210. The first wavelength swept light source 205 and the second wavelength swept light source 210 are operated in accordance with driver signals received from the driver circuit 250. The driver circuit 250 is also communicatively coupled to a trigger input of the signal processing circuit 290 such that the driver circuit 250 provides trigger signals to the signal processing circuit 290. The signal processing circuit 290 uses the trigger signals to maintain proper timing during the processing of the signals received from detector 220 and the generated sequential clock waveforms received from the photodiode 270.

The signal processing circuit 290 thus uses the sequential clock waveforms generated at least in part by the wavelength reference filters 230 and 240 to maintain a regular time interval during the processing of the signal from the detector 220, i.e., the signal from the interferometer 215. In an embodiment, the signal processing circuit 290 includes a field-programmable gate array (FPGA) to process the input signals.

Figure 3:
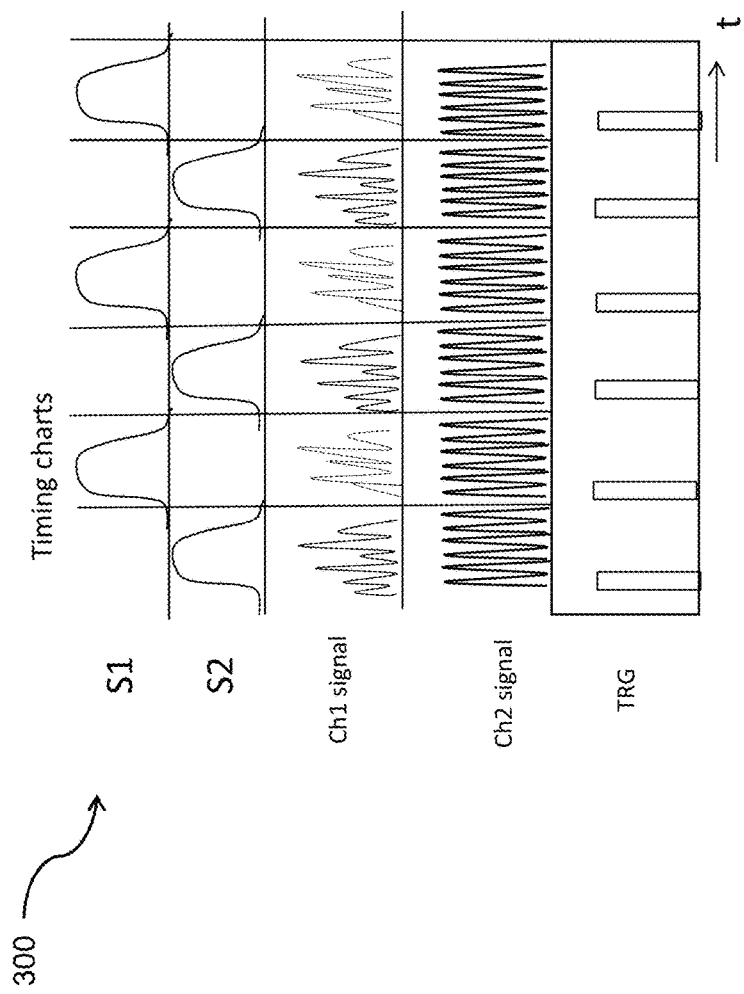
FIG. 3 depicts a graph of timing charts that demonstrate how the various signals associated with the OCT system of FIG. 2 vary over time in accordance with an illustrative embodiment.

FIG. 3 depicts a graph 300 of timing charts that demonstrate how the various signals associated with the OCT system 200 vary over time in accordance with an illustrative embodiment. The graph 300 depicts an output S1 of the first wavelength swept light source 205, an output S2 of the second wavelength swept light source 210, an output signal CH1 of the detector 220, a sequential clock waveform signal CH2, and a trigger signal TRG from the driver circuit 250 over time. As indicated in FIG. 3, the first wavelength swept light source 205 and the second wavelength swept light source 210 alternately emit their respective light beams (e.g., S1 and S2) during successive sweep intervals. As discussed above, the light beams of the first and second wavelength swept light sources 205, 210 may yield backscattered or reflected signals from an imaging sample, e.g., an eye. As an example, the reflected signals may correspond to imaging of an anterior chamber via a first sample path or of a retinal chamber via a second sample path as discussed above with respect to FIG. 1. The reflected signals may be received at a photo-detector, such as the photo-detector 120 shown in FIG. 1 or the detector 220 shown in FIG. 2. The detector may compare the reflected signals to reference signals to generate an output signal CH1 during each sweep interval. Sequential clock waveforms CH2 having equal frequency intervals are also produced each sweep interval. In addition, a trigger signal TRG is also produced at the state of each sweep interval. The CH1, CH2, and TRG signals are received at a signal processing circuit that can generate images of the imaging sample based on these signals.

Figure 4:
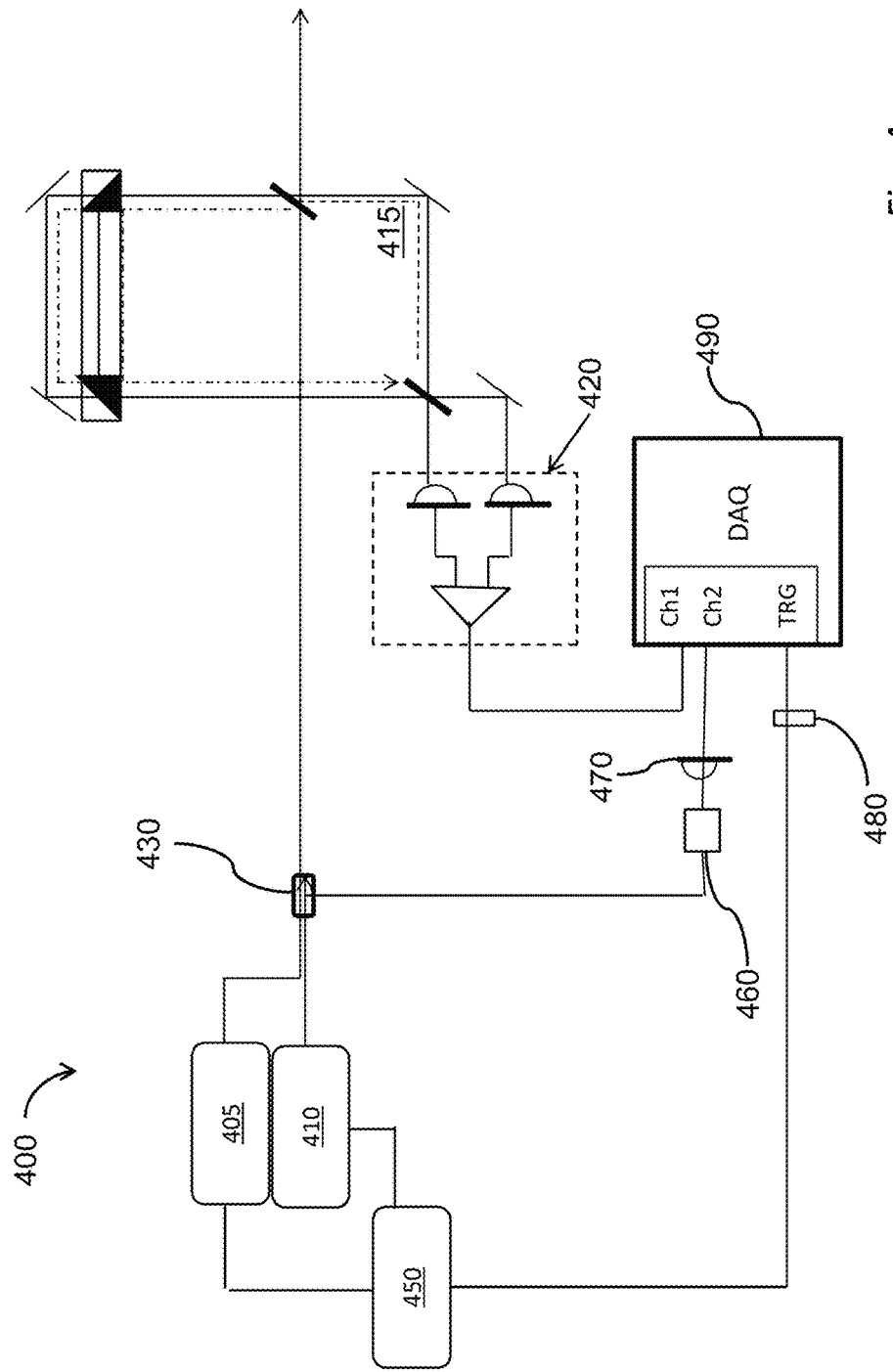
FIG. 4 depicts a representation of an OCT system having a two wavelength swept light sources and a single wavelength reference filter in accordance with an illustrative embodiment.

FIG. 4 depicts a representation of an OCT system 400 having two wavelength swept light sources 405 and 410 and only a single wavelength reference filter 460 in accordance with an illustrative embodiment. In alternative embodiments, fewer, additional, and/or different elements may be present. The first wavelength swept light source 405 emits a first beam having a first wavelength, and the second wavelength swept light source 410 emits a second beam having a second wavelength. In an example embodiment, the first wavelength may be 1.06 microns and the second wavelength may be 1.31 microns. In other embodiments, alternative wavelengths may be used based on imaging requirements. The first beam and the second beam are combined and directed into an interferometer 415 which includes a reference path and a sample path. The first and second beams are directed via respective sample paths to an imaging sample, e.g., an eye. The interferometer 415 and the corresponding sample paths of FIG. 4 are similar to the interferometer 215 and the corresponding sample paths of FIG. 2. Light from the first and second beams that is backscattered and/or reflected from the eye returns to the interferometer along the respective sample paths and is output from the interferometer 415 to a detector 420. Light from the reference path is also output from the interferometer 415 to the detector 420. The detector 420 compares the light from the reference path to the light from the sample paths and outputs a signal based on the comparison. The signal output form the detector 420 is sent to an input channel Ch1 of a signal processing circuit 490. In an embodiment, the signal processing circuit 490 is a data acquisition (DAQ) hardware that interfaces between the signal received from the detector 420 and a computer processing device.

The OCT system 400 further includes a splitter 430. Splitter 430 is positioned between an input to the interferometer 415 and a location at which the first beam from the first wavelength swept light source 405 is combined with the second beam from the second wavelength swept light source 410. According to this configuration, the first beam from the first wavelength swept light source 405 is combined onto a same path with the second beam from the second wavelength swept light source 410 and the combined first and second beams are passed to the splitter 430. The splitter 430 splits a portion of the combined first and second beams onto a separate path that includes a wavelength reference filter 460. In an implementation, the splitter 430 splits only a small portion of the combined first and second beams onto the separate path while allowing a majority of the combined first and second beams to pass to the interferometer 415. For example, in one implementation, approximately ten percent of the light on the combined first and second beams is passed to the wavelength reference filter 460, and approximately ninety percent of the light on the combined first and second beams is passed to the interferometer 415. In other implementations, different percentages of light may be split by splitter 430 based on the design needs of the particular imaging application.

The wavelength reference filter 460 has an equal interval frequency comb. Accordingly, the light output from the wavelength reference filter 430 is equally-spaced in the frequency domain, thus providing equal frequency intervals with which to resample signals received from the detector 420. In an embodiment, the wavelength reference filter 460 may include a Fabry-Perot Etalon filter, a Mach-Zehnder filter, or any other suitable filter known to those of skill in the art. The output from the wavelength reference filter 460 is passed to a photodiode 470 to generate sequential clock waveforms having regular, equal frequency intervals. The sequential clock waveforms are generated by the wavelength reference filter 460 from the combined first and second beams that is split by splitter 430. The sequential clock waveforms correspond to alternately swept wavelength ranges of the first and second wavelength swept light sources 405 and 410. An input channel Ch2 of the signal processing circuit 490 is connected to the output of the photodiode 470 such that the generated sequential clock waveforms are received at the input channel Ch2 of the signal processing circuit 490.

The OCT system 400 also includes a driver circuit 450 that is communicatively coupled to the first wavelength swept light source 405 and the second wavelength swept light source 410. The first wavelength swept light source 405 and the second wavelength swept light source 410 are operated in accordance with driver signals received from the driver circuit 450. The driver circuit 450 is also communicatively coupled to a trigger input of the signal processing circuit 490 such that the driver circuit 450 provides trigger signals to the signal processing circuit 490. The signal processing circuit 490 uses the trigger signals to maintain proper timing during the processing of the signals received from detector 420 and the generated sequential clock waveforms received from the photodiode 470.

The signal processing circuit 490 thus uses the sequential clock waveforms generated at least in part by the wavelength reference filter 460 to maintain a regular time interval during the processing of the signal from the detector 420, i.e., the signal from the interferometer 415. In an embodiment, the signal processing circuit 490 includes a field-programmable gate array (FPGA) to process the input signals.

Figure 5:
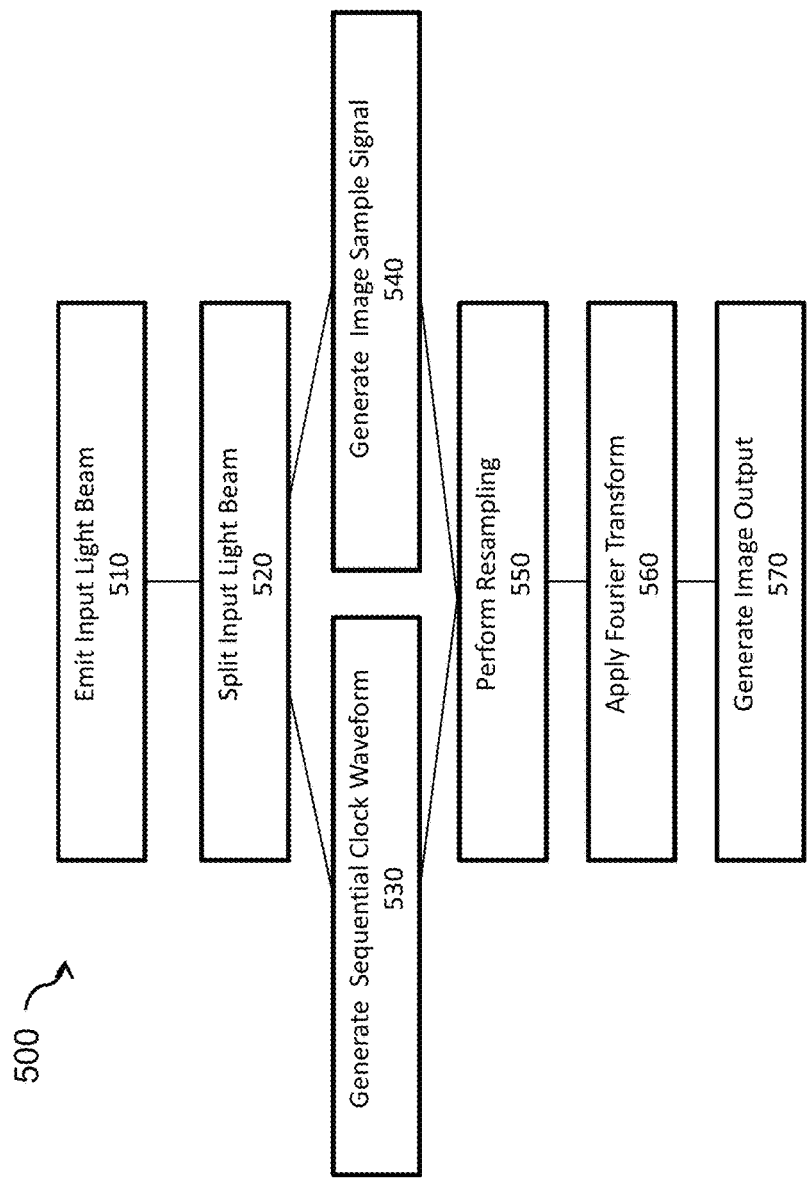
FIG. 5 depicts a flow diagram for a method of analyzing OCT signals in accordance with an illustrative embodiment.

FIG. 5 depicts a flow diagram for a method of analyzing OCT signals in accordance with an illustrative embodiment. The method provides an improved resampling (also called recalibration) scheme that requires only one additional input channel by combining multiple sets of clock waveforms in the optical domain. Such a system greatly reduces the number and complexity of traditional resampling systems that involve multiple, separate light sources that have different nonlinear sweeps.

The method 500 includes emitting first and second light beams from two respective wavelength swept light sources in an operation 510. The first and second light beams have different wavelengths (or different bands of wavelength). By using multiple light beams having different wavelengths, such a system is capable of imaging different portions of an imaging sample, e.g., both the anterior chamber and the retina of an eye may be imaged simultaneously by superimposing the two light paths of different wavelength ranges into one path.

Light from the first and second light beams is split via a splitter in an operation 520. The splitter is located between the wavelength swept light sources and an interferometer. In one embodiment, the light from each of the two wavelength swept light sources may be split before it is combined onto a single path and passed to the interferometer. In another embodiment, the light from each of the two wavelength swept light sources may be combined into a single light bath before being split.

In an operation 530, a portion of the split light is passed to one or more wavelength reference filters to generate sequential clock waveforms. Each of the one or more wavelength reference filters has equal interval frequency combs. In an embodiment, split light from each of the wavelength swept light sources is passed through a respective wavelength reference filter. The light output from each of the respective wavelength reference filters is combined at a combiner to generate the sequential clock waveforms. The generated sequential clock waveforms are passed to a photodiode that converts the waveform to an electrical signal for input into a signal processing circuit.

In another embodiment where the light from the two wavelength swept light sources is combined before being split, the combined split light from the two wavelength swept light sources is passed to a single wavelength reference filter having an equal interval frequency comb. The light output from the single wavelength reference filter is used to generate the sequential clock waveforms. The generated sequential clock waveforms are again passed to a photodiode that converts the waveform to an electrical signal for input into the signal processing.

In an operation 540, an image sample signal is generated via a n interferometer and detector. In an embodiment, the remaining light from first and second light beams that is not split and passed to the wavelength reference filters is instead passed to the interferometer. The interferometer generates multiple reference and sample paths for the light beams. The light on the sample paths is passed to an imaging sample, e.g., an eye, and light that is backscattered or reflected from the imaging sample is returned to the interferometer where it is output and compared by a detector to light from a reference path. Based on this comparison, the detector outputs an image sample signal.

In an operation 550, the signal processing circuit uses the sequential clock waveform signal to resample the image sample signal at equal frequency intervals. In an operation, 560, the signal processing circuit applies a Fourier transform to the resampled signal. In an operation 570, an image corresponding to the imaging sample is created and output based on the transformed, resampled signal.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An optical coherence tomography (OCT) system comprising:
    a first light source configured to emit a first beam having a first wavelength;
    a second light source configured to emit a second beam having a second wavelength;
    an interferometer, wherein the first beam and the second beam are configured to be directed into the interferometer, and further wherein the interferometer comprises:
        a reference path, and
        an interferometer sample path;
    a detector configured to compare light from the reference path with light from the interferometer sample path and produce an imaging sample signal based on the comparison; and
    a first splitter configured to split light from at least one of the first light source and the second light source, wherein the first splitter is located on a light path between the first light source and the interferometer;
    a first wavelength reference filter having an equal interval frequency comb, wherein the wavelength reference filter is configured to produce a sequential clock waveform from light received from the first splitter; and
    a signal processing circuit configured to resample the imaging sample signal based on the sequential clock waveform.

2. The OCT system of claim 1, wherein the first splitter is configured to split light from the first light source, the OCT system further comprising a second splitter configured to split light from the second light source, wherein the second splitter is located between the second light source and the interferometer.

3. The OCT system of claim 2, further comprising a second wavelength reference filter having a second equal interval frequency comb, wherein the second wavelength reference filter is configured to produce a second sequential clock waveform from light received from the second splitter.

4. The OCT system of claim 3, wherein the first wavelength reference filter has a different interval frequency than the second wavelength reference filter.

5. The OCT system of claim 3, further comprising a combiner configured to combine light received from the first wavelength reference filter with light received from the second wavelength reference filter.

6. The OCT system of claim 5, wherein the combiner comprises at least one of a coupler or a dichroic wavelength division multiplexing (WDM) filter.

7. The OCT system of claim 6, wherein the combiner is configured to generate sequential clock waveforms that correspond to alternatively swept wavelength ranges from the first and the second light sources.

8. The OCT system of claim 7, further comprising a photodiode configured to convert the sequential clock waveform from the combiner to an electrical signal and to pass the electrical signal to the signal processing circuit.

9. The OCT system of claim 6, wherein the signal processing circuit is configured to analyze the image sample signal alternately for different time slots based on a trigger signal from a driver circuit and the sequential clock waveform.

10. The OCT system of claim 9, wherein the signal processing circuit is further configured to create two images by selecting specific time slots of the imaging sample signal based on the sequential waveform.

11. The OCT system of claim 1, wherein the first splitter is configured to pass a majority of the light from the first light source to the interferometer and to pass a minority of the light from the first light source to the first wavelength reference filter.

12. The OCT system of claim 1, further comprising a combiner positioned between the first and second light sources and the first splitter, wherein the combiner is configured to combine light from the first and second light sources.

13. The OCT system of claim 1, further comprising a driver circuit connected to the first light source, the second light source, and the signal processing circuit.

14. The OCT system of claim 13, wherein the signal processing circuit is configured to analyze the imaging sample signal alternately for different time slots based on a trigger signal from the driver circuit and sequential clock waveforms generated at least in part from the first wavelength reference filter.

15. The OCT system of claim 1, wherein the signal processing circuit comprises a field-programmable gate array (FPGA).

16. A method comprising:
    emitting, from a first light source, a first beam having a first wavelength;
    emitting, from a second light source, a second beam having a second wavelength;
    splitting the first beam and the second beam;
    passing a first portion of a split beam to an interferometer;

generating, using the interferometer, an image sample form the first portion of the split beam;

passing a second portion of the split beam to a wavelength reference filter;

generating a sequential clock waveform from the second portion of the split beam; and resampling the image sample using the sequential clock waveform.

17. The method of claim 16, wherein generating a sequential clock waveform comprises generating sequential clock waveforms from split portions of both the first and second beams.

18. The method of claim 17, wherein resampling the image sample is performed using the sequential waveforms from the split portions of both the first and second beams.

19. The method of claim 16, wherein the resampling comprises analyzing the image sample alternately for different time slots based on a trigger signal from a driver circuit and the sequential clock waveform.

20. The method of claim 16, further comprising creating two images by selecting specific time slots of the imaging sample based on the sequential clock waveform.

* * * * *